United States Patent [19]

Krstenansky

[11] Patent Number: 5,495,000

[45] Date of Patent: Feb. 27, 1996

[54] ANTICOAGULANT PEPTIDES

[75] Inventor: John L. Krstenansky, Palo Alto, Calif.

[73] Assignee: Merrell Pharmaceuticals Inc., Cincinnati, Ohio

[21] Appl. No.: 432,617

[22] Filed: May 2, 1995

Related U.S. Application Data

[63] Continuation of Ser. No. 971,909, filed as PCT/US91/04658, Jun. 28, 1991, abandoned, which is a continuation of Ser. No. 677,614, Mar. 27, 1991, abandoned, which is a continuation of Ser. No. 557,288, Jul. 24, 1990, abandoned.

[51] Int. Cl.$^6$ .............................. A61K 38/00; C07K 5/00; C07K 7/00; C07K 16/00
[52] U.S. Cl. .............................. 530/327; 530/324; 530/326
[58] Field of Search .............................. 530/324, 326, 530/327; 514/13, 14, 15

[56] References Cited

U.S. PATENT DOCUMENTS 4,792,525  12/1988  Ruoslahti et al. .

FOREIGN PATENT DOCUMENTS

| | | |
|---|---|---|
| 0276014 | 7/1988 | European Pat. Off. . |
| 0347376 | 2/1989 | European Pat. Off. . |
| 0332523 | 9/1989 | European Pat. Off. . |
| 0333356 | 9/1989 | European Pat. Off. . |
| 0341607 | 11/1989 | European Pat. Off. . |
| 0373503 | 6/1990 | European Pat. Off. . |
| 0421367 | 4/1991 | European Pat. Off. . |
| 0421366 | 4/1991 | European Pat. Off. . |
| 9119734 | 12/1991 | European Pat. Off. . |
| 468448 | 1/1992 | European Pat. Off. . |
| 468327 | 1/1992 | European Pat. Off. . |
| 9201712 | 2/1992 | European Pat. Off. . |

OTHER PUBLICATIONS

Krstensnaky J. L. et al., "Development of MDL 28,050, a Small Stable Antithrombin Agent Based on Functional Domain of The Leech Protein, Hirudin", Thrombosis and Haemostasis (Stuttgart) 63(2) 208–214 (1990).

Krstenansky J. L. et al., "Comparison of Hirudin and Hirudin PA C–Terminal Fragments and Related Analogs as Antithromein Agents", Thrombosis Research 52; 137–141, (1988).

Krstenansky, et al., Chemical Abstracts vol. 109:231560t, p. 918, (1988).

Krstenansky J. L. et al., "Characterization of the Interaction of Thrombin with the C–terminal Region of the Leech Anticoagulent Peptide Hirudin", Peptides Chemistry and Biology, Proceed. of 10th American Peptide Sym., May (1987) pp. 447–448.

Hoffmann A. et al., "Inhibition of the Thrombin–Platelet Reaction by Hirudin", Haemostasis 14:164–169 (1984).

Krstenansky J. L. et al., "Anticoagulant Peptides: Nature of the Interaction of the C–Terminal Region of Hirudin with a Noncatalytic Binding Site on Thrombin", J. Med. Chem. 1987, 30, pp. 1688–1691.

Markwardt F. et al., "Comparative Studies on Thrombin Inhibitors in Experimental Microthrombisis", Thrombosis and Haemostasis (Stuttgart) 49 (3) 235–237 (1983).

Minar, et al., abstract of "Local Hirudin Application," Klin Wochenschr 63(4):190–1 (1985).

Maraganore et al., J. Biol. Chem., vol. 264, No. 15, pp. 8692–8698 (1989).

Physicians Desk Reference Edward Barnhart Pub. 45th Ed. pp. 224 and 207 (1991).

Pierschbacher et al., J. Biol. Chem., vol. 262, No. 86, pp. 17294–17298 (1987).

Lam et al., J. Biol. Chem., vol. 262, No. 3, pp. 947–950 (1987).

Church et al., "Chimeric Antithrombin Peptide," J. Biol. Chem., vol. 266, No. 18, pp. 11975–11979 (1991).

Krstenansky, et al., "Antithrombin Properties of C–terminus of Hirudin using Synthetic unsulfated N–acetyl–hirudin 45–65," FEBS Lett. 211 (1) 10–16 (1987).

Bajusz, et al., "Thrombin Inhibition by Hirudin Fragments: Possible Mechanism of Hirudin–Thromein Interaction," Peptides 32:473–476 (1984).

Dodt, et al., "The complete amino acid sequence of hirudin, a thrombin specific inhibitor," FEBS Letters 165(2), 180–84 (1984).

Owen, et al., "N–Terminal Requirements of Small Peptide Anticoagulants Based on Hirudin 54–65," J. Med. Chem., 31, 1009–1011 (1988).

Krstenansky, et al., "Characterization of the Interaction of Thrombin with the Carboxyl–terminal Region of the Leech Anticoagulant Peptide Hirudin," *Peptides: Chemistry and Biology*, 1987, pp. 447–448.

Rydel et al., "The Structure of a Complex of Recombinant Hirudin and Human a–Thrombin" *Science* vol. 249, pp. 277–280 (1990).

Krstenansky et al., "The C–Terminal binding domain of hirullin P18. Antithrombin activity and comparison to hirudin peptides" *FEBS Letters*, vol. 269, No. 2, pp. 425–429 (1990).

Krstenansky et al, *Febs Letters*, vol. 269, No. 2, pp. 425–429 (1990).

*Primary Examiner*—Jill Warden
*Assistant Examiner*—A. M. Davenport
*Attorney, Agent, or Firm*—William R. Boudreaux

[57] ABSTRACT

This invention relates to peptide derivatives which are useful anticoagulant agents.

8 Claims, No Drawings

ANTICOAGULANT PEPTIDES

CROSS-REFERENCE TO RELATED APPLICATION

This is a continuation, of application Ser. No. 07/971,909, filed Dec. 18, 1992, now abandoned (elected under PCT Application Ser. No 91/04658 filed Jun. 28, 1991) Which is a continuation of Application Ser. No. 07/677,614 filed Mar. 27, 1991 now abandoned which is a continuation of Application Ser. No. 07/557,288 filed Jul. 24, 1990 now abandoned which is herein incorporated by reference.

FIELD OF INVENTION

This invention relates to novel peptides which are useful anticoagulant and antiplatelet agents.

BACKGROUND OF INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Prophylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Hirullin P18 is a 61-amino acid hirudin-related protein having potent antithrombin activity. Similar to hirudin, it contains a highly acidic C-terminus of significantly different sequence from any other known hirudin variant. The C-terminal fragment acetyl-hirullin $P18_{40-61}$ has an antithrombin potency similar to that of acetyl-desulfatohirudin-$_{45-65}$. While applicant has discovered that certain amino acids residues of the native sequence are critical to maintaining the antithrombin activity of the fragment, other residues have been found to be less important. Significant differences in the sequences of hirullin $P18_{54-61}$ from hirudin$_{59-65}$ suggest a different mode of interaction with thrombin. Nevertheless, the C-terminal functional domain represented by hirullin $P18_{50-61}$ appears to be comparable to hirudin$_{55-65}$ in terms of its binding to thrombin and its functional role in the protein.

Moreover, several reports have described the ability of the oligopeptide Arg-Gly-Asp and related peptides to inhibit the platelet-dependent thrombus formation. Y. Cadroy, et al., J. Clin. Invest. 84, 939–944 (1989). Applicant has discovered that when this oligopeptide is linked to the amino terminal end of the antithrombotic hirullin fragments, the resulting peptide analogs have significant and useful antiplatelet activity in addition to the antithrombotic activity. This new class of compounds should provide for a useful adjunct therapy due to the dual mode of action.

SUMMARY OF THE INVENTION

Peptide derivatives of the formula

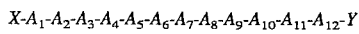

wherein A is an amino terminal residue selected from hydrogen, one or two alkyl groups of from 1 to 6 carbon atoms, one or two acyl groups of from 2 to 10 carbon atoms, carbobenzyloxy, $H_2NC(=NH)$—, or a t-butyloxy carbonyl group;

$A_1$ is a bond or is a peptide fragment containing from 1 to 11 residues of any amino acid;

$A_2$ is a bond or is a group of the formula

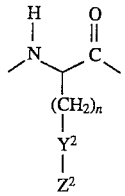

wherein $Y_2$=O, $NR_2'$, S, bond, $Z^2$=—$SO_3H$,

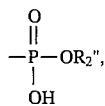

n is an integer of from 1 to 5 and wherein $R_2'$ and $R_2''$ are each independently an H or a ($C_1$–$C_4$)alkyl group;

$A_3$ is Phe, SubPhe, β-(2- and 3-thienyl)alanine, β-(2-and 3-furanyl)alanine, β-(2-, 3-, and 4-pyridyl)alanine, β-(benzothienyl-2- and 3-yl)alanine, β-(1- and 2-naphthyl)alanine, Tyr, Tyr(Me) and Trp;

$A_4$ is a bond or is a group of the formula

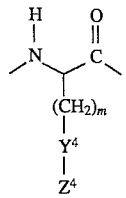

wherein $Y_4$=O, $NR_2'$, S, bond, $Z_4$=—$SO_3H$,

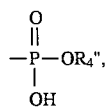

m is an integer of from 1 to 5 and wherein $R_4'$ and $R_2''$ are each an H or a ($C_1$–$C_4$)alkyl group;

$A_5$ is any amino acid;

$A_6$ is Tyr, Trp, Phe, Leu, Nle, Ile, Val, Cha and Pro;

$A_7$ is Pro, Ser, Ala, and Thr;

$A_8$ is Tyr, tyr, Trp, trp, Phe, phe, Leu, leu, Nle, nle, Ile, ile, Val, val, Cha, cha, Pro, and pro;

$A_9$ is any amino acid;

$A_{10}$ is any amino acid;

$A_{11}$ is Tyr, Trp, Phe, Leu, Nle, Ile, Val, Cha and Pro;

$A_{12}$ is a bond or is a peptide fragment containing from one to ten residues of any amino acid; and Y is a carboxy terminal residue selected from OH, $C_1$–$C_6$ alkoxy, amino, mono- or di-($C_1$–$C_4$) alkyl substituted amino, or benzylamino;

or a pharmaceutically acceptable salt thereof are useful anticoagulant agents.

DETAILED DESCRIPTION OF THE INVENTION

The following common abbreviations of the amino acids are used throughout this specification:

Gly - glycine
Ala - alanine
Val - valine
Leu - leucine
Ile - isoleucine
Cha - cyclohexylalanine
Orn - ornithine
Pro - proline
Phe - phenylalanine
Trp - tryptophan
Met - methionine
Ser - serine
Thr - threonine
Cys - cysteine
Tyr - tyrosine
Asn- asparagine
Gln- glutamine
Asp - aspartic acid
Glu - glutamine acid
Lys - lysine
Hly - homolysine
Arg - arginine
Har - homoarginine
His - histidine
Nle - norleucine
Hyp - hydroxyproline
Glt- glutaryl
Mal - maleyl
Npa -β-(2-naphthyl)alanine
3,4-dehydroPro - 3,4-dehydroproline
Tyr(SO₃H) - tyrosine sulfate
Pgl - phenylglycine
NMePgl - N-methyl-phenylglycine
Sar - sarcocine (N-methylglycine)
pSuPhe - para substituted phenylalanine
SubPhe - ortho, meta, or para, mono- or di- substituted phenylalanine
DAla - D-alanine
Ac - acetyl
Suc - succinyl
pClPhe - para-chloro-phenylalanine
pNO₂Phe - para-nitro-phenylalanine
Tyr(Me) - O-methyltyrosine An alkyl group and the alkyl portion of an alkoxy group is taken to include straight, branched, or cyclic alkyl groups, for example, methyl, ethyl, propyl, isopro- pyl, butyl, isobutyl, tert-butyl, pentyl, isopentyl, sec-pentyl, cyclopentyl, hexyl, isohexyl, cyclohexyl and cyclopentylmethyl. An acyl group of from 2 to 10 carbon atoms is taken to include straight, branched, cyclic, saturated and unsaturated acyl groups having 1 or 2 carbonyl moieties per group, for example, acetyl, benzoyl succinyl, maleyl, and glutaryl. A halogen group is a fluoro, chloro, bromo or iodo group.

The term "any amino acid" as used herein includes the naturally occurring amino acids as well as other "non-protein" α-amino acids commonly utilized by those in the peptide chemistry arts when preparing synthetic analogs of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" α-amino acids are norleucine, norvaline, alloisoleucine, homoarginine, thiaproline, dehydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines substituted at the ortho, meta, or paraposition of the phenyl moiety with one or two of the following, a $(C_1-C_4)$ alkyl, $(C_1-C_4)$ alkoxy, halogen, or nitro groups or substituted with a methylenedioxy group, β- 2- and 3-thienylalanine, β-2- and 3-furanylalanine, β-2-, 3-, and 4-pyridylalanine, β-(benzothienyl-2- and 3-yl)alanine, β-(1- and 2-naphthyl)alanine, O-alkylated derivates of serine, threonine, or tyrosine, S-alkylated cysteine, the O-sulfate ester of tyrosine, 3,5-diiodotyrosine and the D-isomers of the naturally occurring amino acids. The term "any amino acid" is also intended to encompass those naturally occurring and non-protein a-amino acids of the formula

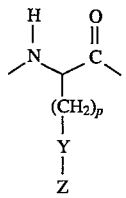   2

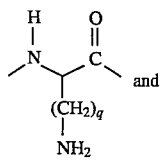 and   3

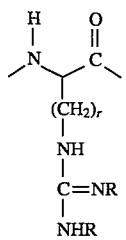   4 wherein Y is either $Y^2$ or $Y^4$ and Z is either $Z^2$ or $Z^4$ as defined above and p, q, and r are each an integer of from 1 to 5 and wherein R is a hydrogen or a $(C_1-C_4)$alkyl group.

The term "lipophilic amino acid" includes Tyr, Phe, Leu, Nle, Ile, Val, His and Pro.

The natural amino acids with the exception of glycine, contain a chiral carbon atom. Unless otherwise specifically indicated, the optically active amino acids, referred to herein, are of the L-configuration. For example, any of the amino acids of the $A_1$ or $A_{12}$ group can be of the D- or L-configuration. As is customary, the structure of peptides written out herein is such that the amino terminal end is on the left side of the chain and the carboxy terminal end is on the right side of the chain. As is also customary when using the three-letter code for the amino acids, a three-letter code begining with an upper case letter indicates the L-confuguration and a three-letter code beginning with a lower-case letter indicates the D-configuration.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

While all the compounds of formula 1 possess anticoagulant activity, certain compounds of formula 1 additionally possess significant antiplatelet activity. In particular, those compounds of formula 1 wherein $A_2$ is other than a bond and wherein $A_1$ is a dipeptide fragment of formula 5 or 6

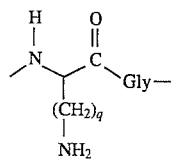

5

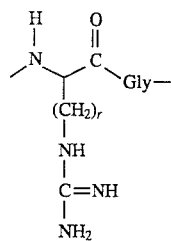

6 wherein q and r are each an integer of from 1 to 5 or wherein $A_1$ is a peptide fragment containing from 3 to 11 residues wherein the carboxy terminal end of the peptide fragment is a dipeptide fragment of formula 5 or 6 are platelet aggregation inhibitors.

As with any generic group of chemical compounds, certain groups are preferred. Of the compounds of formula 1 not having significant antiplatlet activity, applicants prefer those peptide derivatives wherein X is hydrogen, acetyl, $H_2NC(=NH)—$, or succinyl. Also preferred are those formula 1 compounds wherein $A_1$ is Thr-Pro-Lys-Arg-Gln-Thr-Ser-Gly-Pro-, Seq ID No 1
Pro-Lys-Arg-Gln-Thr-Ser-Gly-Pro-, Seq ID No 2
Lys-Arg-Gln-Thr-Ser-Gly-Pro-, Seq ID No 3
Arg-Gln-Thr-Ser-Gly-Pro-, Seq ID No 4
Gln-Thr-Ser-Gly-Pro-, Seq ID No 5
Thr-Ser-Gly-Pro-, Seq ID No 6
Ser-Gly-Pro-,
Gly-Pro-,
Pro-, or
a bond;

$A_2$ is preferably a group of the formula

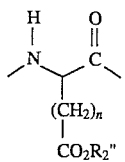

wherein n is an integer of from 1 to 5 and
wherein $R_2''$ is an H or a $(C_1-C_4)$alkyl group;
$A_3$, Phe, Tyr, Tyr(OCH$_3$), or Trp;
$A_4$, Glu or Asp;
$A_5$, Glu or Pro;
$A_6$, Phe or Cha;
$A_7$, Ser or Pro;
$A_8$, Leu;
$A_9$, Asp;
$A_{10}$, Asp;
$A_{11}$, Ile, Cha, or Val;
$A_{12}$, a bond, Glu, glu or -Glu-Gln; and
Y, OH or NH$_2$.

Especially preferred are those peptide derivatives of formula 1 having significant antiplatelet activity wherein either X is succinyl, hydrogen, or $H_2NC(=NH)—$ and $A_1$ is a dipeptide fragment selected from a 5-guanidopentanoyl-Gly- group or -Arg-Gly-, -Har-Gly-, -Lys-Gly-, and -Hly-Gly- as well as where $A_2$, is Asp;
$A_3$, Phe, Tyr, Tyr(Me), or Trp;
$A_4$, Glu;
$A_5$, Glu or Pro;
$A_6$, Phe or Cha;
$A_7$, Ser;
$A_8$, Leu;
$A_9$, Asp;
$A_{10}$, Asp;
$A_{11}$, Ile or Val;
$A_{12}$, a bond; and
Y, OH or NH$_2$.

Of those compounds of formula 1 not having significant antiplatelet activity, applicants prefer those peptide derivatives wherein X is hydrogen, acetyl, $H_2NC(=NH)—$, or succinyl. Also preferred are those formula 1 compounds wherein $A_1$ is a bond or a compound of formula 5 or 6.
$A_2$ is preferably a group of the formula

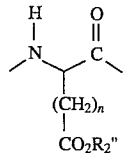

wherein n is an integer of from 1 to 5 and
wherein $R_2''$ is an H or a $(C_1-C_4)$alkyl group;
$A_3$, Phe, Tyr, Tyr(Me), or Trp;
$A_4$, Glu or Asp;
$A_5$, Glu or Pro;
$A_6$, Phe or Cha;
$A_7$, Ser;
$A_8$, Leu;
$A_9$, Asp;
$A_{10}$, Asp;
$A_{11}$, Ile, Cha, or Val;
$A_{12}$, a bond or -Glu-Gln-; and
Y, OH o r NH$_2$.

The peptide analogs of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of an automated peptide sythesizer. In this procedure an α-amino protected amino acid is bound to a resin support. The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky, et al., *Chem. Ind.* (*London.*) 38, 1597–98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem Acta*, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxy-methylated phenylacetamidomethyl (PAM) resin can be used and is commercially available.

Following the coupling of the a-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitro-phenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzyl- carbonyl, p-bromobenzyloxycarbonyl, p-methoxybenzyloxycarbonyl, 1-(p-biphenylyl)-1-methylethoxycarbonyl, α, α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxy-benzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium- 3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.*, 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After the desired amino acid sequence has been obtained, the peptide is removed from the resin. This can be done by hydrolysis such as by treatment of the resin bound polypeptide with a solution of dimethyl sulfide, p-cresol and thiocresol in dilute aqueous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

These groups can be removed by procedures well known in the art. Typically protecting group removal is done after the peptide chain synthesis is complete but the protecting groups can be removed at any other appropriate time.

The anticoagulant and antiplatelet dose of a peptide analog of this invention is from 0.2 mg/kg to 250 mg/kg of patient body weight per day depending on the patient, the severity of the thrombotic condition to be treated and the peptide analog selected. The suitable dose for a particular patient can be readily determined. Preferably from 1 to 4 daily doses would be administered typically with from 5 mg to 100 mg of active compound per dose.

Anticoagulant therapy is indicated for the treatment and prevention of a variety of thrombotic conditions, particularly coronary artery and cerebrovascular disease as well as for the treatment of, for example, coronary occlusion, by dissolving existing clots. Antiplatelet therapy is indicated for the prevention of reoccurance of myocardial infarction and stroke. Those experienced in this field are readily aware of the circumstances requiring anticoagulant and antiplatelet therapy. The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containg a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

EXAMPLE 1

Preparation of Ser-Asp-Phe-Glu-Glu-Phe-Ser-Leu-Asp-Asp-Ile-Glu-Gln-OH Seq ID No 7

The peptide was synthesized by solid-phase methods using 0.1 mmol of a 0.66 mmol/g Boc-Gln-PAM resin. Double symmetrical anhydride couplings were performed with 2.0 mmol Nα-Boc-amino acid (Peptides International). The side chain protection utilized was: Asp(Chx), Ser(Bzl), Glu(Bzl). Upon completion of the synthesis the Nα-Boc protection was removed with 50% trifluoroacetic acid in methylene chloride. The resin was washed three times with methylene chloride, neutralized with three washings of 10% diisopropylethylamine in methylene chloride, washed three times with methylene chloride, and dried in vacuo. The peptide was deprotected and cleaved from the resin with HF containing 2% anisole at 0° C., for 35 min. The HF was removed in vacuo at 0° C., the peptide precipitated with ethyl ether, extracted from the resin with 30% aqueous acetic acid and lyophilized.

The peptide was purified by desalting on a 92×2.6 cm Sephadex G-15 column in 5% aqueous acetic acid and lyophilized. Preparative HPLC was performed on a $C^{18}$ Vydac 218TP1010 (250 ×10 mm) column with 24% acetonitrile in 0.1% aqueous trifluoroacetic acid at 5 ml/min. The major peak was collected and lyophilized. Homogeneity was determined by HPLC and TLC.

The peptides of examples 2–8 have been prepared in substantially the same way.

EXAMPLE 2

Asp-Phe-Glu-Glu-Phe-Ser-Leu-Asp-Asp-Ile-Glu-Gln-OH
Seq ID No 8

EXAMPLE 3

Phe-Glu-Glu-Phe-Ser-Leu-Asp-Asp-Ile-Glu-Gln-OH
Seq ID No 9

EXAMPLE 4

Suc-Phe-Glu-Glu-Phe-Ser-Leu-Asp-Asp-Ile-Glu-Gln-OH
Seq ID No 10

EXAMPLE 5

Suc-Phe-Glu-Pro-Phe-Ser-Leu-Asp-Asp-Ile-Glu-Gln-OH
Seq ID No 11

EXAMPLE 6

Suc-Phe-Glu-Glu-phe-Pro-Leu-Asp-Asp-Ile-Glu-Gln-OH
Seq ID No 12

EXAMPLE 7

Suc-Phe-Glu-Glu-Phe-Ser-Leu-Asp-Asp-Cha-Glu-Gln-OH
Seq ID No 13

EXAMPLE 8

Arg-Gly-Asp-Phe-Glu-Glu-Phe-Ser-Leu-Asp-Asp-Ile-Glu-Gln-OH
Seq ID No 14

| EXAMPLE No. | Amino Acids Analysis (6N HCl Hydrolysis; 24 Hrs at 106° C.) | | | | | | | |
|---|---|---|---|---|---|---|---|---|
| | Asx | Ser | Glx | Arg | Gly | Ile | Leu | Phe |
| 1 | 3.00 | 1.90 | 3.91 | | | 0.80 | 1.03 | 2.06 |
| 2 | 3.10 | 1.02 | 4.00 | | | 0.79 | 1.03 | 2.06 |
| 3 | 2.03 | 0.96 | 3.92 | | | 0.79 | 1.03 | 2.03 |
| 4 | 2.06 | 0.97 | 3.80 | | | 0.66 | 1.04 | 2.09 |
| 5 | 2.00 | 0.90 | 2.63 | | | 0.73 | 1.10 | 2.27 |
| 6 | 2.06 | | 3.80 | | | 0.67 | 1.05 | 2.09 |
| 7 | 2.00 | 0.96 | 4.02 | | | | 1.00 | 1.98 |

| EXAMPLE No. | Amino Acids Analysis (6N HCl Hydrolysis; 24 Hrs at 106° C.) | | | | | | | |
|---|---|---|---|---|---|---|---|---|
| | Asx | Ser | Glx | Arg | Gly | Ile | Leu | Phe |
| 8 | 3.12 | 0.96 | 3.77 | 0.98 | 1.02 | -/64 | 1.04 | 2.06 |

| Physical Characteristics | |
|---|---|
| EXAMPLE NO. | FAB-MS (M + H) |
| 1 | 1573.6 |
| 2 | 1486.6 |
| 3 | 1372.1 |
| 4 | 1471.3 |
| 5 | 1439.6 |
| 6 | 1481.4 |
| 7 | 1511.0 |

| Physical Characteristics | |
|---|---|
| EXAMPLE NO. | FAB-MS (M + H) |
| 8 | 1699.8 |

| Fibrin-Clot Inhibition | |
|---|---|
| EXAMPLE NO. | IC$_{50}$ (μM) |
| 1 | 4.2 |
| 2 | 9.3 |
| 3 | 2.3 |
| 4 | 2.7 |
| 5 | 1.8 |
| 6 | 2.3 |
| 7 | 7.1 |
| 8 | 5.2 |

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Thr Pro Lys Arg Gln Thr Ser Gly Pro
    1               5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Pro Lys Arg Gln Thr Ser Gly Pro
    1               5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Lys Arg Gln Thr Ser Gly Pro
    1               5

( 2 ) INFORMATION FOR SEQ ID NO:4:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

Arg Gln Thr Ser Gly Pro
1               5

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Gln Thr Ser Gly Pro
    1               5

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Thr Ser Gly Pro
    1

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Ser Asp Phe Glu Glu Phe Ser Leu Asp Asp Ile Glu Gln
    1               5                   10

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Asp Phe Glu Glu Phe Ser Leu Asp Asp Ile Glu Gln
    1               5                   10

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Phe Glu Glu Phe Ser Leu Asp Asp Ile Glu Gln
1               5                   10

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Phe at location 1 is
            N- substituted with a succinyl group"

( x i ) SEQUENCE DESCRIPTION: SEQ ID NO:10:

Phe Glu Glu Phe Ser Leu Asp Asp Ile Glu Gln
1               5                   10

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Phe at location 1 is
            N- substituted with a succinyl group"

( x i ) SEQUENCE DESCRIPTION: SEQ ID NO:11:

Phe Glu Pro Phe Ser Leu Asp Asp Ile Glu Gln
1               5                   10

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Phe at location 1 is
            N- substituted with a succinyl group"

( x i ) SEQUENCE DESCRIPTION: SEQ ID NO:12:

Phe Glu Glu Phe Pro Leu Asp Asp Ile Glu Gln
1               5                   10

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide (ix) FEATURE:
    (A) NAME/KEY: Modified-site
    (B) LOCATION: 1
    (D) OTHER INFORMATION: /note="Phe at location 1 is N-substituted with a succinyl group"

(ix) FEATURE:
    (A) NAME/KEY: Modified-site
    (B) LOCATION: 9
    (D) OTHER INFORMATION: /note="Xaa at location 9 is a cyclohexylalanine"

(xi) SEQUENCE DESCRIPTION: SEQ ID NO:13:

Phe Glu Glu Phe Ser Leu Asp Asp Xaa Glu Gln
1               5                   10

(2) INFORMATION FOR SEQ ID NO:14:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:14:

Arg Gly Asp Phe Glu Glu Phe Ser Leu Asp Asp Ile Glu Gln
1               5                   10

What is claimed is:

1. A peptide of the formula Ser-Asp-Phe-Glu-Glu-Phe-Ser-Leu-Asp-Asp-Ile-Glu-Gln-OH.

2. A peptide of the formula Asp-Phe-Glu-Glu-Phe-Ser-Leu-Asp-Asp-Ile-Glu-Gln-OH.

3. A peptide of the formula Phe-Glu-Glu-Phe-Ser-Leu-Asp-Asp-Ile-Glu-Gln-OH.

4. A peptide of the formula Suc-Phe-Glu-Glu-Phe-Ser-Leu-Asp-Asp-Ile-Glu-Gln-OH.

5. A peptide of the formula Suc-Phe-Glu-Pro-Phe-Ser-Leu-Asp-Asp-Ile-Glu-Gln-OH.

6. A peptide of the formula Suc-Phe-Glu-Glu-Phe-Pro-Leu-Asp-Asp-Ile-Glu-Gln-OH.

7. A peptide of the formula Suc-Phe-Glu-Glu-Phe-Ser-Leu-Asp-Asp-Cha-Glu-Gln-OH.

8. A peptide of the formula Arg-Gly-Asp-Phe-Glu-Glu-Phe-Ser-Leu-Asp-Asp-Ile-Glu-Gln-OH.

* * * * *

UNITED STATES PATENT AND TRADEMARK OFFICE
CERTIFICATE OF CORRECTION

PATENT NO. : 5,495,000
DATED : February 27, 1996
INVENTOR(S) : John L. Krstenansky It is certified that error appears in the above-identified patent and that said Letters Patent is hereby corrected as shown below:

Column 2, Line 20 Patent reads "  " and should read -- --.

Column 2, Line 44 Patent reads " 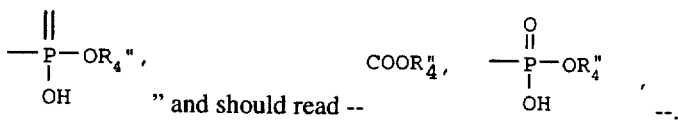 " and should read -- --.

Column 2, Line 46 Patent reads "$R_2''$" and should read --$R_4''$--.
Column 3, Line 41 Patent reads "pSuPhe" and should read --pSubPhe--.
Column 7, Line 32 Patent reads "a-amino" and should read --α-amino--.
Column 9, Line 27 Patent reads "containg" and should read --containing--.
Column 10, Line 44 Patent reads "-phe-Pro" and should read -- -Phe-Pro- --.
Column 11, Line 5 Patent reads
"(1) GENERAL INFORMATION
    (iii) NUMBER OF SEQUENCES: 14
(2) INFORMATION FOR SEQ ID NO:1:"
and should read
--(1) GENERAL INFORAMTION:
    (i) APPLICANT: Krstenansky, John L
    (ii) TITLE OF INVENTION: Anticoagulant Peptides
    (iii) NUMBER OF SEQUENCES: 14
    (iv) CORRESPONDENCE ADDRESS:
        (A) ADDRESSEE: Marion Merrell Dow Inc.
        (B) STREET: 2110 East Galbraith Rd.
        (C) CITY: Cincinnati P.O. Box 156300
        (D) STATE: Ohio
        (E) COUNTRY: USA
        (F) ZIP: 45215-6300

UNITED STATES PATENT AND TRADEMARK OFFICE
CERTIFICATE OF CORRECTION

PATENT NO. : 5,495,000
DATED : February 27, 1996
INVENTOR(S) : John L. Krstenansky It is certified that error appears in the above-identified patent and that said Letters Patent is hereby corrected as shown below:

(v) COMPUTER READABLE FORM:
    (A) MEDIUM TYPE: Floppy disk
    (B) COMPUTER: IBM PC compatible
    (C) OPERATING SYSTEM: PC-DOS/MS-DOS
    (D) SOFTWARE: PatentIn Release #1.0, Version #1.25

(vi) CURRENT APPLICATION DATA:
    (A) APPLICATION NUMBER: US 07/971,909
    (B) FILING DATE: 18-DEC-1992
    (C) CLASSIFICATION:

(vii) PRIOR APPLICATION DATA:
    (A) APPLICATION NUMBER: US 07/557,288
    (B) FILING DATE: 24-JUL-1990

(vii) PRIOR APPLICATION DATA:
    (A) APPLICATION NUMBER: WO PCT/US91/04658
    (B) FILING DATE: 28-JUN-1991

(viii) ATTORNEY/AGENT INFORMATION:
    (A) NAME: Boudreaux, William R
    (B) REGISTRATION NUMBER: 35,796
    (C) REFERENCE/DOCKET NUMBER: M01556 US-A (ix) TELECOMMUNICATION INFORMATION:

UNITED STATES PATENT AND TRADEMARK OFFICE
CERTIFICATE OF CORRECTION

PATENT NO. : 5,495,000

DATED : February 27, 1996

INVENTOR(S) : John L. Krstenansky

It is certified that error appears in the above-identified patent and that said Letters Patent is hereby corrected as shown below:

(A) TELEPHONE: (513) 948-6566
      (B) TELEFAX: (513) 948-7961
      (C) TELEX: 214320
(2)   INFORMATION FOR SEQ ID NO:1:--.

Signed and Sealed this

Twenty-first Day of April, 1998

Attest:

BRUCE LEHMAN

*Attesting Officer*        *Commissioner of Patents and Trademarks*